(12) United States Patent
Sawyer (10) Patent No.: US 10,336,162 B2
(45) Date of Patent: Jul. 2, 2019

(54) HVAC SYSTEM WITH ODOR ABSORBENT REGENERATION

(71) Applicant: FORD GLOBAL TECHNOLOGIES, LLC, Dearborn, MI (US)

(72) Inventor: Robert Steven Sawyer, Farmington Hills, MI (US)

(73) Assignee: Ford Global Technologies LLC, Dearborn, MI (US)

( * ) Notice: Subject to any disclaimer, the term of this patent is extended or adjusted under 35 U.S.C. 154(b) by 205 days.

(21) Appl. No.: 15/634,359

(22) Filed: Jun. 27, 2017

(65) Prior Publication Data
US 2018/0370335 A1 Dec. 27, 2018

(51) Int. Cl.
*B01D 53/04* (2006.01)
*B60H 3/00* (2006.01)
(Continued)

(52) U.S. Cl.
CPC .......... *B60H 3/0085* (2013.01); *A61L 9/014* (2013.01); *B01D 46/0036* (2013.01); *B01D 46/0038* (2013.01); *B01D 46/0063* (2013.01); *B01D 46/448* (2013.01); *B01D 53/04* (2013.01); *B01D 53/0438* (2013.01); *B01J 20/20* (2013.01); *B60H 1/00492* (2013.01); *A61L 2209/16* (2013.01); *A61L 2209/22* (2013.01); *B01D 2259/40088* (2013.01); *B01D 2259/4566* (2013.01); *B60H 2003/0057* (2013.01)

(58) Field of Classification Search
CPC ............ B01D 46/0035; B01D 46/0038; B01D 46/0063; B01D 46/448; B01D 53/04; B01D 53/0438; B01D 2253/102; B01D 2257/90; B01D 2258/06; B01D 2259/4566; B01D 2259/40088; A61L 9/014; A61L 2209/16; A61L 2209/22; B01J 20/20; B60H 1/00492; B60H 3/0085; B60H 2003/0057
USPC .......... 95/14, 18, 26, 148; 96/112, 115, 143, 96/144, 146
See application file for complete search history.

(56) References Cited

U.S. PATENT DOCUMENTS

| 4,530,817 A | 7/1985 | Holter et al. |
| 5,273,487 A | 12/1993 | Dauvergne |

(Continued)

FOREIGN PATENT DOCUMENTS

| DE | 19955253 A1 | 6/2001 |
| EP | 0715878 B1 | 1/2002 |

(Continued)

OTHER PUBLICATIONS

English Machine Translation of JP2000042092A.
(Continued)

*Primary Examiner* — Frank M Lawrence, Jr.
(74) *Attorney, Agent, or Firm* — Vichit Chea; King & Schickli PLLC (57) ABSTRACT

An HVAC system is provided for a motor vehicle. That HVAC system includes a heater plenum, a fresh air inlet, an odor absorbent and a regeneration blower assembly that is connected between the heater plenum and the fresh air inlet. The HVAC system further includes a controller configured to regenerate the odor absorbent when an ignition system of the motor vehicle is switched off and a coolant temperature of the motor vehicle exceeds a predetermined coolant temperature required for odor absorbent regeneration.

18 Claims, 6 Drawing Sheets

(51) Int. Cl.
  *B60H 1/00* (2006.01)
  *B01D 46/00* (2006.01)
  *B01D 46/44* (2006.01)
  *A61L 9/014* (2006.01)
  *B01J 20/20* (2006.01)

(56) References Cited

U.S. PATENT DOCUMENTS

| | | | |
|---|---|---|---|
| 5,620,367 A * | 4/1997 | Khelifa | B01D 53/261 |
| | | | 454/156 |
| 5,681,218 A * | 10/1997 | Kishi | B60H 3/0085 |
| | | | 454/139 |
| 5,938,523 A * | 8/1999 | Khelifa | B60H 3/0633 |
| | | | 454/156 |
| 6,080,059 A | 6/2000 | Kim | |
| 6,197,097 B1 | 3/2001 | Ertl et al. | |
| 6,314,949 B1 | 11/2001 | DeGrazia, Jr. et al. | |
| 7,013,656 B2 | 3/2006 | Yanagimachi et al. | |
| 10,183,556 B2 * | 1/2019 | Sawyer | B60H 3/0633 |
| 2002/0139251 A1 | 10/2002 | Simmons | |
| 2006/0112702 A1 * | 6/2006 | Martin | B60H 1/00378 |
| | | | 62/180 |
| 2016/0288043 A1 | 10/2016 | Meirav et al. | |
| 2017/0050497 A1 * | 2/2017 | Sawyer | B60H 3/0633 |

FOREIGN PATENT DOCUMENTS

| | | |
|---|---|---|
| JP | 2000042092 A | 2/2000 |
| JP | 2000127756 A | 5/2000 |
| WO | 1998018540 A1 | 5/1998 |

OTHER PUBLICATIONS

English Machine Translation of JP2000127756A.
Non-Final Office Action dated Jul. 3, 2018 for U.S. Appl. No. 15/611,938, filed Jun. 2, 2017.
English Machine Translation of DE19955253A1.

* cited by examiner

HVAC SYSTEM WITH ODOR ABSORBENT REGENERATION

TECHNICAL FIELD

This document relates generally to the motor vehicle equipment field and, more particularly, to a heating, ventilating and air-conditioning (HVAC) system and method for regenerating odor absorbent.

BACKGROUND

Today's motor vehicles are commonly equipped with air filters including odor absorbent material, such as activated carbon, to trap odors and prevent them from permeating the passenger cabin of the motor vehicle. Under certain conditions, odors previously trapped in the odor absorbent may outgas into the passenger cabin through the ducts of the HVAC system so that when the doors are opened and people enter the vehicle, unpleasant odors are present.

This document relates to a new and improved HVAC system and method that provides for regenerating the odor absorbent in the motor vehicle HVAC system. The HVAC system is also specifically adapted to push the odors from the regenerated odor absorbent material outside the vehicle and into the ambient environment after the owner/occupants have left the vehicle.

SUMMARY

In accordance with the purposes and benefits described herein, an HVAC system is provided for a motor vehicle. That HVAC system is configured to regenerate an odor absorbent in the motor vehicle HVAC system. That HVAC system includes a heater plenum, a fresh air inlet, an odor absorbent, a regeneration blower assembly and a controller. The regeneration blower assembly is connected between the heater plenum and the fresh air inlet of the HVAC system. The controller is configured to regenerate the odor absorbent when an ignition system of the motor vehicle is switched off and a coolant temperature of the motor vehicle exceeds a predetermined coolant temperature required for odor absorbent regeneration.

The regeneration blower assembly may include a blower fan controlled by the controller. The regeneration blower assembly may include a regeneration door displaceable between an opened position and a closed position in response to the controller. The regeneration blower assembly may also include a first duct connecting the blower fan with the heater plenum and a second duct connecting the blower fan with the fresh air inlet.

The controller may be operatively connected to the fresh air inlet door. In such an embodiment, the controller may be configured to open the regeneration door, open the fresh air inlet door and activate the blower fan for a predetermined period of time when the ignition switch is off and the predetermined coolant temperature is exceeded. As a result, air is drawn from a passenger cabin of the motor vehicle through the heater plenum where that air is warmed. The warmed air is then drawn through the first duct to the blower fan and then forced by the blower fan through the second duct and the odor absorbent. As a result, the odor absorbent is regenerated and odor producing contaminants released from the odor absorbent are discharged into the ambient atmosphere from the fresh air inlet.

In another possible embodiment, the controller is configured to open the regeneration door, open the fresh air inlet door and activate the blower fan for a predetermined period of time when the ignition system is switched off, the passenger cabin of the motor vehicle is unoccupied and the predetermined coolant temperature is exceeded. As a result, air is drawn through the heater plenum where the air is warmed. That warmed air is then drawn through the first duct to the blower fan and then forced by the blower fan through the second duct and the odor absorbent. The odor absorbent is regenerated and odor producing contaminants, previously captured by the odor absorbent, are released and discharged into the ambient environment from the fresh air inlet.

The controller may be configured to close the regeneration door, close the fresh air inlet and deactivate the blower fan after the predetermined period of time has expired.

In accordance with another aspect, a motor vehicle is provided that is equipped with the HVAC system described in this document.

In accordance with yet another aspect, a method is provided for regenerating an odor absorbent in an HVAC system of a motor vehicle. That method comprises the steps of: (a) monitoring, by a temperature monitoring device, a coolant temperature of the motor vehicle and (b) heating and regenerating, by a controller, the odor absorbent using heat from a heater core of the HVAC system when the coolant temperature exceeds a predetermined coolant temperature required for odor regeneration.

The method may also include the step of monitoring, by ignition monitoring device, an ignition system of the motor vehicle and only heating and regenerating the odor absorbent when the ignition system is switched off. In addition, the method may include the step of performing the heating and regenerating for a predetermined period of time after an ignition system of the motor vehicle is switched off.

Still further, the method may include the step of performing the heating and regenerating for a predetermined period of time after an ignition system of the motor vehicle is switched off and a passenger cabin of the motor vehicle is determined to be unoccupied.

The method may also include the step of using a dedicated blower fan to draw air through the heater plenum of the HVAC system and then force that heated or warmed air through the odor absorbent to regenerate the odor absorbent. Further, the method may include the step of discharging the air and odors entrained therein through a fresh air inlet of the HVAC system following regeneration.

The method may also include the steps of opening the regeneration door leading to the blower fan and opening a fresh air inlet door prior to energizing the blower fan for heating and regenerating. Further, the method may include the steps of closing the regeneration door, closing the fresh air inlet door and de-energizing the blower fan after the predetermined time has expired. The method may also include the step of utilizing a controller to (a) open and close the regeneration door and the fresh air inlet door and (b) energize and de-energize the blower fan.

In the following description, there are shown and described several preferred embodiments of the HVAC system and method. As it should be realized, the system and method are capable of other, different embodiments and their several details are capable of modification in various, obvious aspects all without departing from the regeneration system and method as set forth and described in the following claims. Accordingly, the drawings and descriptions should be regarded as illustrative in nature and not as restrictive.

BRIEF DESCRIPTION OF THE DRAWING FIGURES

The accompanying drawing figures incorporated herein and forming a part of the specification, illustrate several aspects of the regeneration apparatus and method and together with the description serve to explain certain principles thereof. In the drawing figures:

FIG. 1b is a schematic illustration of the control system for the regeneration apparatus illustrated in FIG. 1a.

Reference will now be made in detail to the present preferred embodiments of the regeneration apparatus and method, examples of which are illustrated in the accompanying drawing figures.

DETAILED DESCRIPTION

Figure 1A:
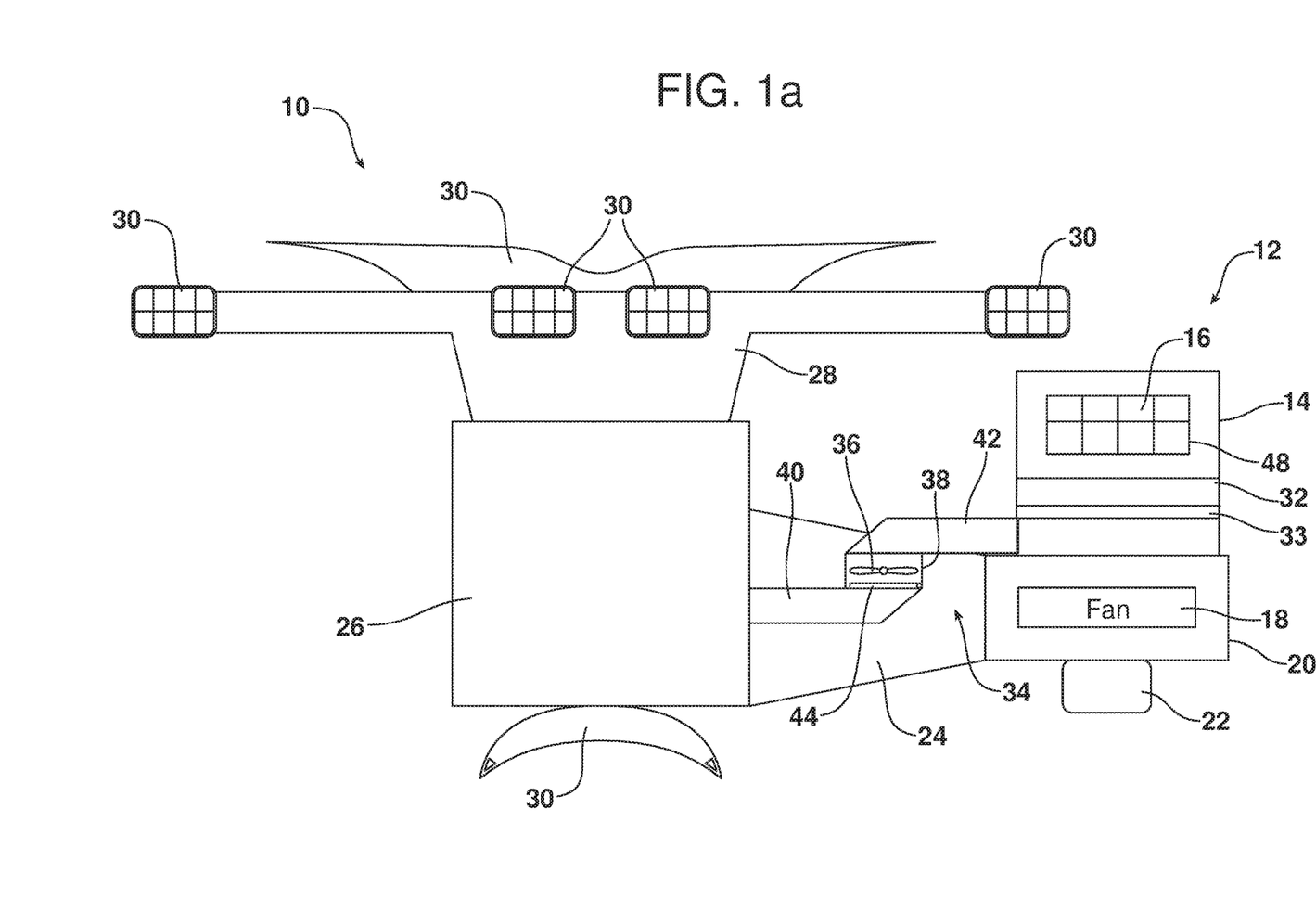
FIG. 1a is a schematic illustration of a motor vehicle HVAC system including the regeneration apparatus that is the subject matter of this document.
Figure 1B:
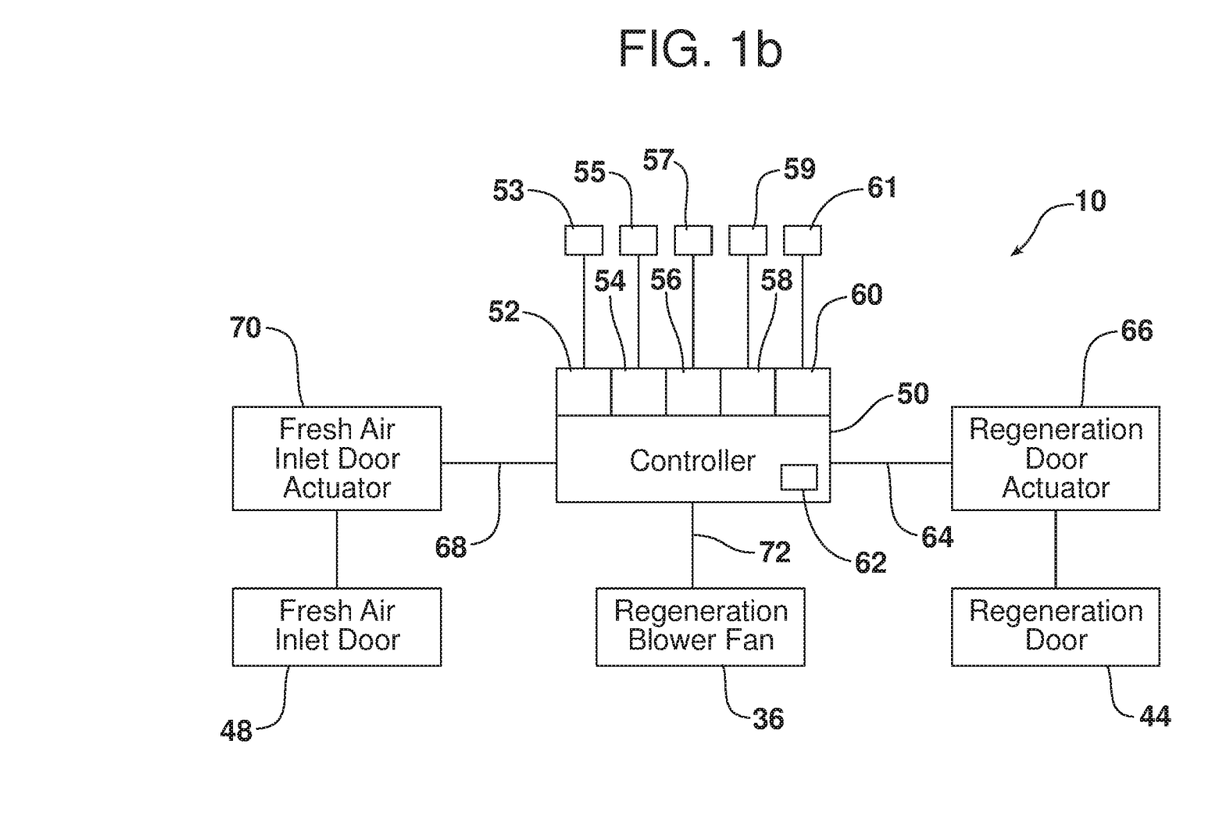

Reference is now made to FIGS. 1a and 1b, which schematically illustrate the apparatus 10 for regenerating an odor absorbent 33, such as activated carbon, in a motor vehicle HVAC system, generally designated by reference number 12. That HVAC system 12 includes an inlet duct 14 having a fresh air inlet opening 16, a circulation fan 18 held in a fan housing 20 and powered by a fan motor 22, a ventilation manifold 24 for delivering air from the circulation fan 18 to the heater plenum 26 and duct work 28 to deliver treated air to various outlet vents 30 which deliver that air to the passenger cabin of the motor vehicle. A particulate air filter 32, including an odor absorbent 33 such as activated carbon, is provided in the inlet duct 14 between the fresh air inlet opening 16 and the fan housing 20. Thus, air being drawn into the HVAC system 12 of the motor vehicle through the fresh air inlet opening 16 passes through the air filter 32 before being forced by the circulation fan 18 into the cabin of the motor vehicle. This allows odors to be withdrawn from the airstream and captured by the odor absorbent 33 provided in the particulate filter 32 so that those odors are prevented from reaching the occupants of the motor vehicle in the passenger cabin.

The regeneration apparatus 10 that is the subject matter of this document includes a regeneration blower assembly generally designated by reference number 34. As illustrated in FIG. 1a, that regeneration blower assembly 34 is connected between the heater plenum 26 and the fresh air inlet duct 14 of the HVAC system 12.

More specifically, the regeneration blower assembly 34 includes a dedicated regeneration blower fan 36 held in a fan compartment 38. A first duct 40 connects the blower fan 36 and the fan compartment 38 with the heater plenum 26, while a second duct 42 connects the blower fan 36 with the fresh air inlet duct 14. In addition, the regeneration blower assembly 34 also includes a regeneration door 44 that is displaceable between an opened position and a closed position in order to control the flow of air between the first duct 40 and the fan compartment 38. The HVAC system 12 includes a similar door, the fresh air inlet door 48 that is utilized to open and close the fresh air inlet opening 16.

As illustrated in FIG. 1b, the regeneration apparatus 10 also includes a controller 50. The controller 50 may take the form of a dedicated microprocessor, computing device or electronic control unit (ECU). Thus, the controller 50 may comprise one or more processors, one or more memories and one or more network interfaces that all communicate with each other over a communication bus.

The controller 50 includes a first data input 52 for receiving data respecting the status of the ignition system of the motor vehicle from an engine ignition status monitoring device 53. The controller 50 also includes a second data input 54 for receiving data respecting the revolutions being turned by the engine that powers the motor vehicle from an engine revolution monitoring device 55. The controller 50 also includes a third data input 56 for receiving data respecting status of the coolant temperature of the engine that powers the motor vehicle from an engine coolant temperature monitoring device 57. The odor absorbent regeneration cycle is not initiated unless the engine coolant temperature is above a predetermined temperature necessary to promote regeneration of the odor absorbent 33.

In addition, the controller 50 includes a fourth data input 58 receiving data respecting the occupancy of the motor vehicle. Occupancy status data may be provided by an occupancy status monitoring device 59 that monitors the status of the vehicle door locks, seatbelt sensors, seat occupancy sensors including pressure sensors in the seats, infrared sensors, internal vehicle cameras for monitoring the presence of motor vehicle occupants, motion sensors or the like.

Still further, the controller 50 also includes a fifth data input 60 for monitoring the charge status of the battery of the motor vehicle from a battery charge status monitoring device 61. In addition, the controller 50 also includes an internal timer 62.

As further illustrated in FIG. 1b, the controller 50 is operatively connected through the control line 64 to a regeneration door actuator 66 that displaces the regeneration door 44 between opened and closed positions. As further illustrated, the controller 50 is also connected through the control line 68 to a fresh air inlet door actuator 70. The fresh air inlet door actuator 70 functions to displace the fresh air inlet door 48 between opened and closed positions.

As is also illustrated in FIG. 1b, the controller 50 is connected via the control line 72 to the dedicated regeneration blower fan 36. The controller 50 is configured to open the regeneration door 44, open the fresh air inlet door 48 and activate the regeneration blower fan 36 for a predetermined period of time based upon the operation of the timer 62 when the ignition system of the motor vehicle is switched off so that air from the passenger cabin of the motor vehicle is drawn through the heater plenum 26 where that air is warmed. Next, the regeneration blower fan 36 draws that warmed air through the first duct 40 past the open regeneration door 44 into the fan compartment 38. The blower fan 36 then forces that warmed air through the second duct 42 and through the particulate air filter 32, including an odor absorbent 33 such as activated carbon.

As the warmed air passes through the particulate air filter 32, the warmed air comes into intimate contact with the odor absorbent 33. Heat from the warmed air causes the odor absorbent 33 to release previously absorbed odors which are then entrained in the air stream, thereby regenerating the odor absorbent 33. The air stream, which now entrains the odors, is then forced by the blower fan 36 past the open fresh air inlet door 48 through the fresh air inlet opening 16 into the ambient environment outside of the motor vehicle passenger cabin. Thus, it should be appreciated that odors are prevented from outgassing into the passenger cabin through the HVAC system.

As should be further appreciated, the controller 50 is also configured to close the regeneration door 44, close the fresh air inlet door 48 and deactivate the dedicated blower fan 36 after the predetermined period of time measured by the internal timer 62 has elapsed.

As should be appreciated, the regeneration apparatus 10 operates in accordance with a method for regenerating odor absorbent 33 in an HVAC system of a motor vehicle. That method may be broadly described as including the steps of monitoring, by temperature monitoring device 57, a coolant temperature of the motor vehicle and heating and regenerating, by the controller 50, the odor absorbent 33 using heat from a heater core or plenum of the HVAC system when the coolant temperature exceeds a predetermined temperature required for odor absorbent 33 regeneration. More specifically, the method may be described as including the step of performing the heating and regenerating for a predetermined period of time after an ignition system of the motor vehicle is switched off.

In some embodiments, the method includes the step of performing the heating and regenerating for a predetermined period of time only after the motor vehicle ignition is switched off and the passenger cabin of the motor vehicle is determined to be unoccupied.

Further, the method may include using a dedicated blower fan 36 to draw air through the heater plenum 26 of the HVAC system 12 and then forcing that air through the odor absorbent 33 to regenerate the odor absorbent 33. Still further, the method may include discharging the air and odors entrained therein through the fresh air inlet opening 16 of the HVAC system following regeneration. Thus, it should be appreciated that the method includes opening a regeneration door 44 leading to the blower fan 36 and opening the fresh air inlet door 48 prior to energizing the blower fan 36 for heating and regenerating. Further, the method includes closing the regeneration door 44 and closing the fresh air inlet door 48 and de-energizing the blower fan 36 after the predetermined time has elapsed. As described, all this is done utilizing the controller 50 which (a) opens and closes the regeneration door 44 and the fresh air inlet door 48 by controlling operation of the door actuators 66, 70 and (b) energizes and de-energizes the motor of the blower fan 36.

Figure 2A:
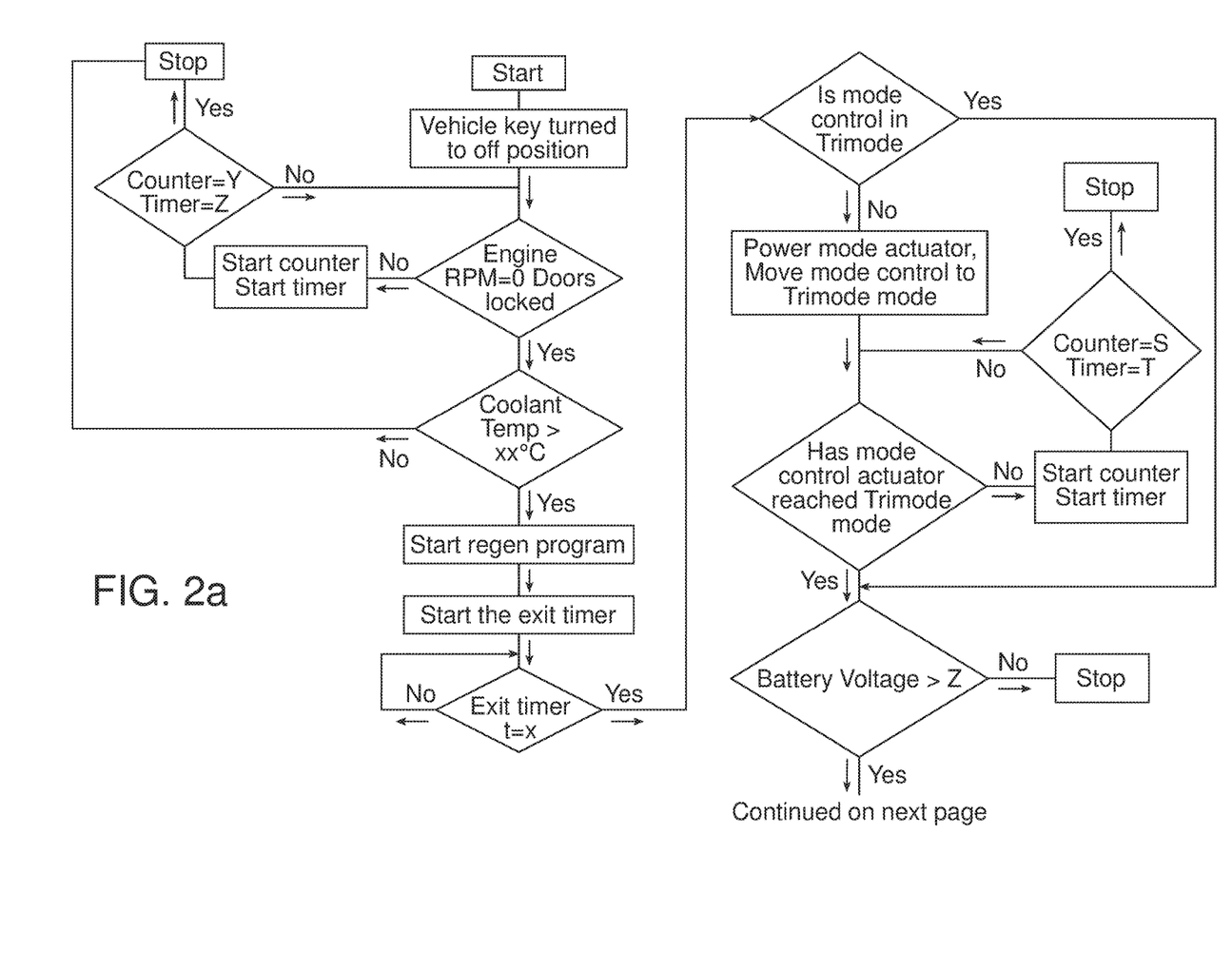
FIGS. 2a-2c are an operations flowchart for the apparatus to aid in illustrating the method that is the subject matter of this document.
Figure 2B:
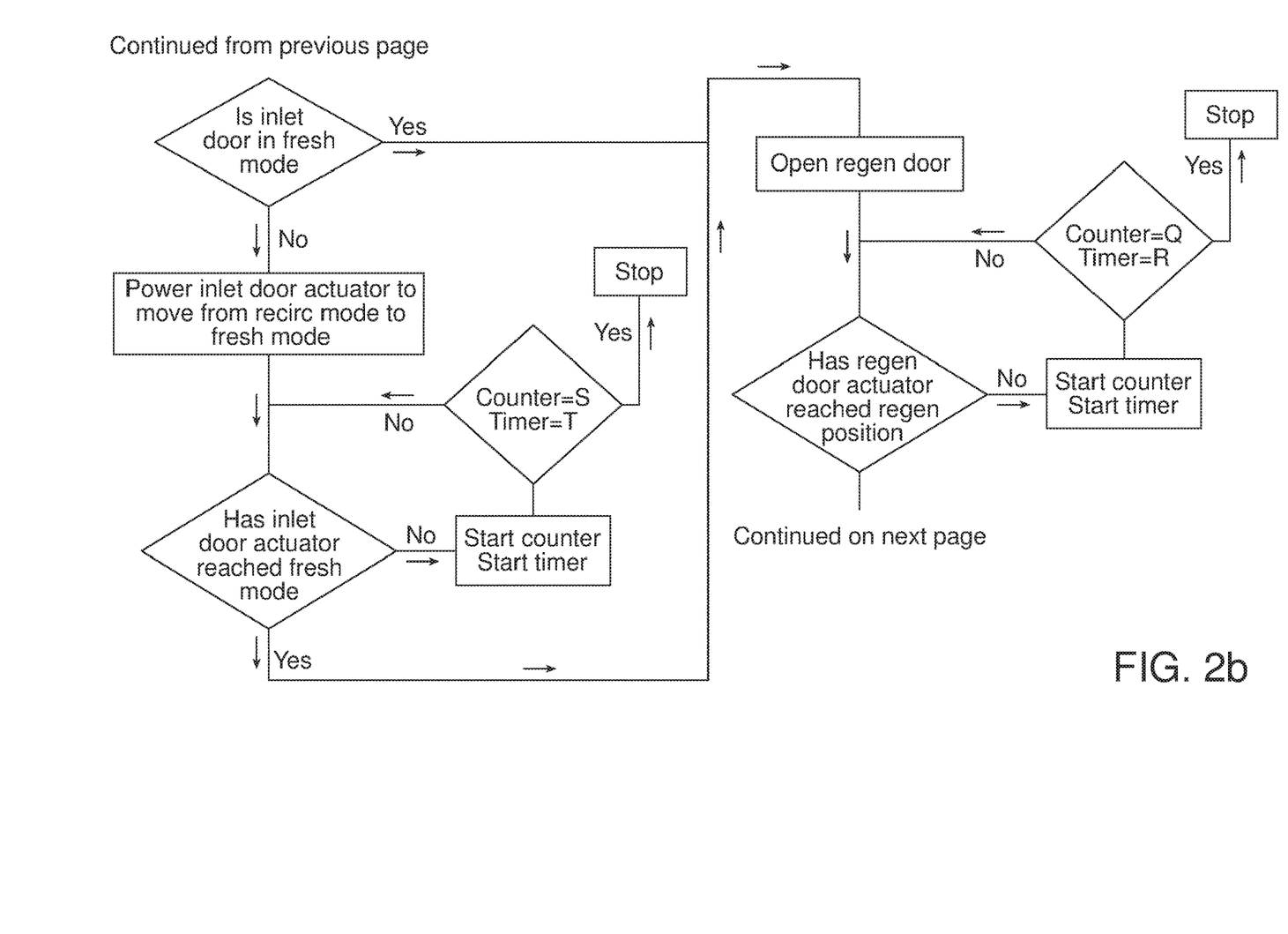
Figure 2C:
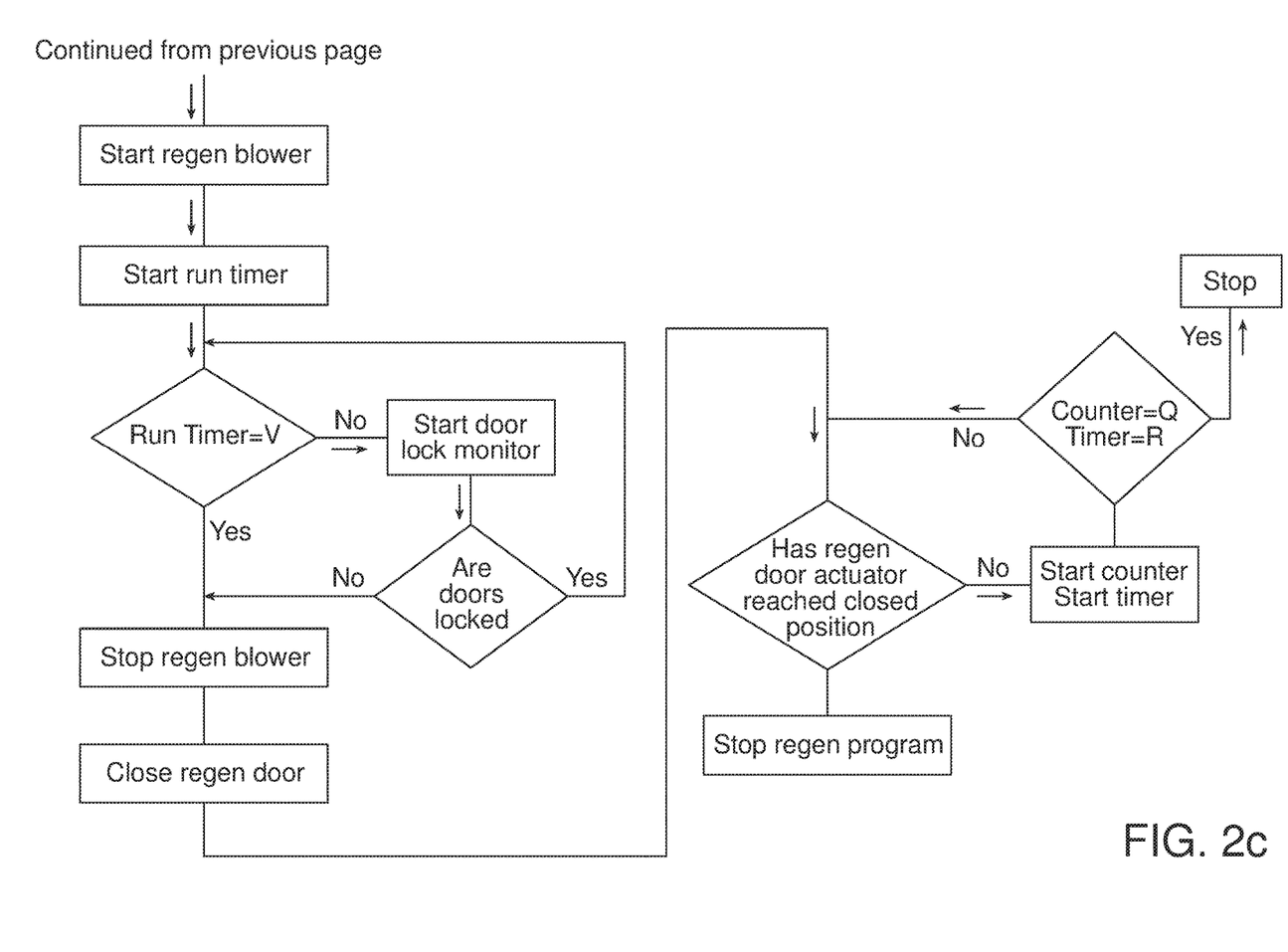

Reference is now made to FIGS. 2a-2c which, taken together, illustrate one possible operations flowchart for the regeneration apparatus 10. As illustrated in FIG. 2a, the regeneration method is initiated when the vehicle key is turned to the off position. This is indicated to the controller at the data input 52. The controller then monitors the data inputs 52, 56 and 58 to confirm that the engine is shut off (engine RPM is equal to zero if data input 54 is used), the coolant temperature is above a predetermined coolant temperature required to regenerate the odor absorbent 33 and the vehicle is no longer occupied (indicated, for example by one of the occupancy status data sources referenced above). Upon receiving confirmation that the engine is off, the coolant temperature is above the predetermined temperature and the passenger cabin is unoccupied, the controller 50 initiates the regeneration process. Toward this end, the controller 50 determines whether the HVAC system is in the tri-mode position wherein all outlet vents 30 including the window defroster vents, instrument panel vents and floor events are open. If not, the controller 50 takes the necessary steps to open all outlet vents 30 of the HVAC system 12 so as to allow the freest possible flow of air between the motor vehicle cabin and the regeneration blower fan 36.

As further illustrated in FIG. 2a, the controller 50 also checks the fifth data input 58 to confirm that the battery is at a sufficient voltage or charge to allow operation of the regeneration apparatus 10 without significant depletion of the battery.

Next, as illustrated in FIG. 2b, the controller 50 confirms the status of the fresh air inlet door 48 and opens that door if it is closed by means of the fresh air inlet door actuator 70. Next, the controller 50 opens the regeneration door 44 by means of the regeneration door actuator 66.

Next, as illustrated in FIG. 2c, the controller 50 activates the regeneration blower fan 36 which is run for a predetermined period of time based upon the timer 62. When the predetermined period of time has elapsed, the controller 50 deactivates the regeneration blower fan 36 and closes the regeneration door 44 through operation of the regeneration door actuator 66. The regeneration program is then stopped. However, it should be appreciated that for certain applications and systems, the controller 50 would also close the fresh air inlet door 48 if it had been previously closed prior to the initiation of the regeneration program.

Figure 3:
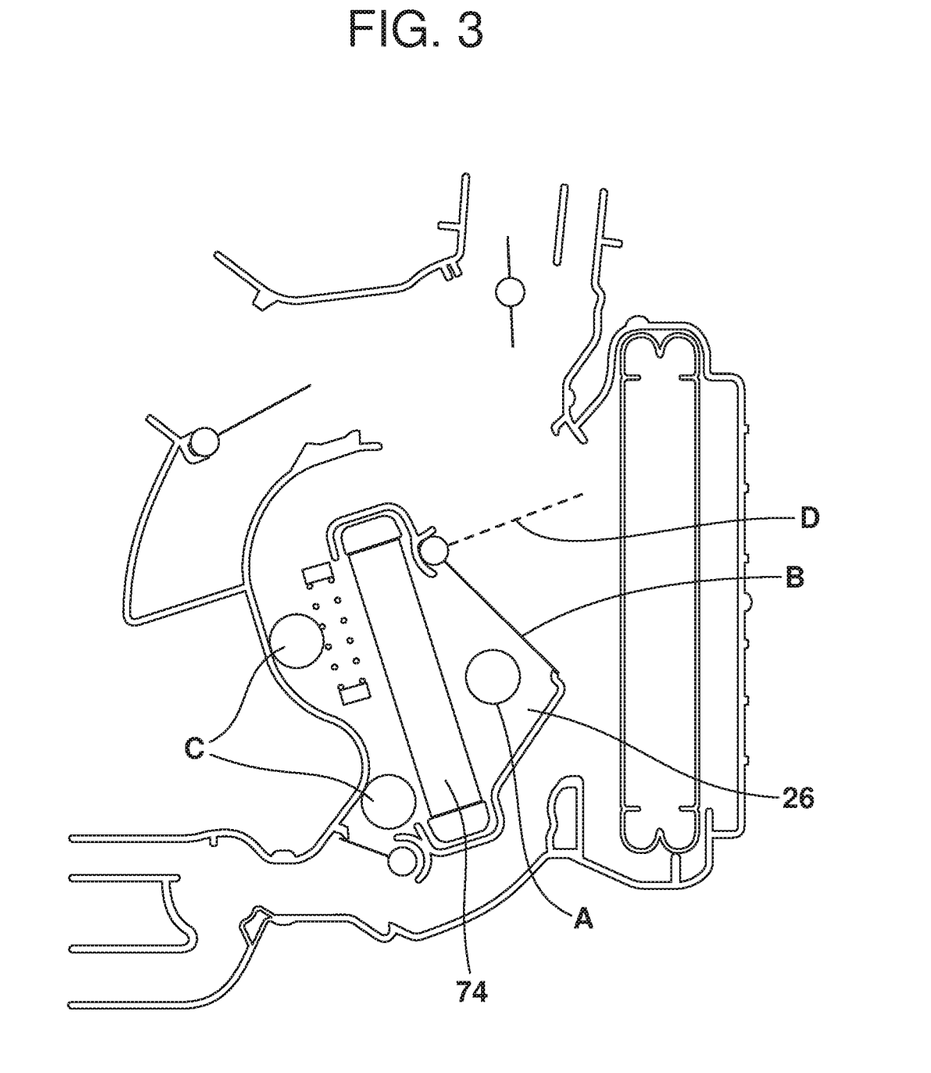
FIG. 3 is a schematic illustration that shows various alternative positions for connection of the first or takeoff duct of the regeneration apparatus to the heater plenum of the motor vehicle HVAC system.

Reference is now made to FIG. 3 which is a detailed cross-sectional view of the heater plenum 26. Reference letter A illustrates a preferred position for the connection of the first duct 40 of the regeneration apparatus 10 in the heater plenum 26 just upstream from the heater core 74 while the reference letter B illustrates a preferred position for the temperature blend door during the regeneration process.

Reference letter C illustrates two possible alternative positions for connection of the first duct 40 to the heater plenum 26. When the first or intake duct 40 is at either of the positions C, it is preferred that the temperature blend door be positioned as illustrated at reference letter D.

The foregoing has been presented for purposes of illustration and description. It is not intended to be exhaustive or to limit the embodiments to the precise form disclosed. Obvious modifications and variations are possible in light of the above teachings. All such modifications and variations are within the scope of the appended claims when interpreted in accordance with the breadth to which they are fairly, legally and equitably entitled.

What is claimed:

1. An HVAC system for a motor vehicle, comprising:
a heater plenum;
a fresh air inlet;
an odor absorbent;
a regeneration blower assembly connected between said heater plenum and said fresh air inlet of said HVAC system; and
a controller configured to regenerate said odor absorbent when an ignition system of said motor vehicle is switched off and a coolant temperature of said motor vehicle exceeds a predetermined coolant temperature required for odor absorbent regeneration.

2. The HVAC system of claim 1, wherein said regeneration blower assembly includes a blower fan controlled by said controller.

3. The HVAC system of claim 2, wherein said regeneration blower assembly includes a regeneration door displaceable between an opened position and a closed position in response to said controller.

4. The HVAC system of claim 3, wherein said regeneration blower assembly includes a first duct connecting said blower fan with said heater plenum and a second duct connecting said blower fan with said fresh air inlet.

5. The HVAC system of claim 4, wherein said controller is operatively connected to a fresh air inlet door.

6. The HVAC system of claim 5, wherein said controller is configured to open said regeneration door, open said fresh air inlet door, and activate said blower fan for a predetermined period of time when said ignition system is switched off and said predetermined coolant temperature is exceeded so that air from a passenger cabin of said motor vehicle is drawn through said heater plenum where the air is warmed, drawn through said first duct to the blower fan and then forced by said blower fan through said second duct and said odor absorbent, regenerating said odor absorbent and then discharged from said fresh air inlet.

7. The HVAC system of claim 5, wherein said controller is configured to open said regeneration door, open said fresh air inlet door, and activate said blower fan for a predetermined period of time when said ignition system is switched off, a passenger cabin of said motor vehicle is unoccupied and said predetermined coolant temperature is exceeded so that air from the passenger cabin of said motor vehicle is drawn through said heater plenum where the air is warmed, drawn through said first duct to the blower fan and then forced by said blower fan through said second duct and said odor absorbent, regenerating said odor absorbent and then discharged from said fresh air inlet.

8. The HVAC system of claim 7, wherein said controller is configured to close said regeneration door, close said fresh air inlet door and deactivate said blower fan after said predetermined period of time has expired.

9. The motor vehicle equipped with the HVAC system of claim 1.

10. A method of regenerating an odor absorbent in an HVAC system of a motor vehicle, comprising:
monitoring, by temperature monitoring device, a coolant temperature of said motor vehicle; and
heating and regenerating, by a controller, said odor absorbent using heat from a heater core of said HVAC system when said coolant temperature exceeds a predetermined coolant temperature required for odor absorbent regeneration.

11. The method of claim 10, including monitoring, by ignition monitoring device, an ignition system of said motor vehicle and only heating and regenerating said odor absorbent when said ignition system is switched off.

12. The method of claim 10, including performing said heating and regenerating for a predetermined period of time after an ignition system of said motor vehicle is switched off.

13. The method of claim 10, including performing said heating and regenerating for a predetermined period of time after an ignition system of said motor vehicle is switched off and a passenger cabin of said motor vehicle is determined to be unoccupied.

14. The method of claim 13, including using a dedicated blower fan to draw air through a heater plenum of said HVAC system and then force that air through said odor absorbent to regenerate said odor absorbent.

15. The method of claim 14, including discharging said air and odors entrained therein through a fresh air inlet of said HVAC system following regeneration.

16. The method of claim 15, including opening a regeneration door leading to said blower fan and opening a fresh air inlet door prior to energizing said blower fan for heating and regenerating.

17. The method of claim 16, including closing said regeneration door, closing said fresh air inlet door and de-energizing said blower fan after said predetermined period of time has expired.

18. The method of claim 17, including utilizing said controller to open and close said regeneration door and said fresh air inlet door and energize and de-energize said blower fan.

* * * * *